United States Patent
Grüne et al.

(10) Patent No.: US 9,957,208 B2
(45) Date of Patent: May 1, 2018

(54) PROCESS FOR PREPARING 1,3-BUTADIENE FROM N-BUTENES BY OXIDATIVE DEHYDROGENATION

(71) Applicants: BASF SE, Ludwigshafen (DE); Linde AG, Munich (DE)

(72) Inventors: Philipp Grüne, Mannheim (DE); Oliver Hammen, Wintersheim (DE); Rainer Eckrich, Schifferstadt (DE); Jan Pablo Josch, Neustadt (DE); Christian Walsdorff, Ludwigshafen (DE); Andre Biegner, Munich (DE); Gregor Bloch, Herrsching (DE); Heinz Boelt, Wolfratshausen (DE); Hendrik Reyneke, Munich (DE); Christine Toegel, Neubiberg (DE); Ulrike Wenning, Pullach (DE)

(73) Assignees: BASF SE (DE); Linde AG (DE)

( * ) Notice: Subject to any disclaimer, the term of this patent is extended or adjusted under 35 U.S.C. 154(b) by 0 days. days.

(21) Appl. No.: 15/503,189

(22) PCT Filed: Aug. 11, 2015

(86) PCT No.: PCT/EP2015/068436
§ 371 (c)(1),
(2) Date: Feb. 10, 2017

(87) PCT Pub. No.: WO2016/023892
PCT Pub. Date: Feb. 18, 2016

(65) Prior Publication Data
US 2017/0233313 A1 Aug. 17, 2017

(30) Foreign Application Priority Data
Aug. 12, 2014 (EP) ...................................... 14180700

(51) Int. Cl.
*C07C 5/48* (2006.01)
*C07C 7/00* (2006.01)
(Continued)

(52) U.S. Cl.
CPC ................ *C07C 5/48* (2013.01); *C07C 7/005* (2013.01); *C07C 7/08* (2013.01); *C07C 7/09* (2013.01); *C07C 7/11* (2013.01); *C07C 2523/887* (2013.01)

(58) Field of Classification Search
CPC ......... C07C 11/167; C07C 5/48; C07C 7/005; C07C 7/08; C07C 7/09; C07C 7/11;
(Continued)

(56) References Cited

U.S. PATENT DOCUMENTS 3,911,039 A    10/1975  Grasselli et al.
3,932,551 A    1/1976   Grasselli et al.
(Continued)

FOREIGN PATENT DOCUMENTS

DE    2440329 A1    3/1975
DE    2447825 A1    8/1975
(Continued)

OTHER PUBLICATIONS

International Search Report for PCT/EP2015/068436 dated Oct. 16, 2015.
(Continued)

*Primary Examiner* — Sharon Pregler
(74) *Attorney, Agent, or Firm* — Drinker Biddle & Reath LLP

(57) ABSTRACT

The invention relates to a process for preparing butadiene from n-butenes, comprising the steps of:
A) providing an input gas stream a comprising n-butenes,
(Continued)

B) feeding the input gas stream a comprising n-butenes and a gas containing at least oxygen into at least one oxidative dehydrogenation zone and oxidatively dehydrogenating n-butenes to butadiene, giving a product gas stream b comprising butadiene, unconverted n-butenes, water vapor, oxygen, low-boiling hydrocarbons and high-boiling secondary components, with or without carbon oxides and with or without inert gases;

Ca) cooling the product gas stream b by contacting with a cooling medium in at least one cooling zone, the cooling medium being at least partly recycled and having an aqueous phase and an organic phase of an organic solvent, wherein the organic solvent is selected from the group consisting of toluene, o-, m- and p-xylene, mesitylene, mono-, di- and triethylbenzene, mono-, di- and triisopropylbenzene and mixtures thereof, and the mass ratio of the aqueous phase to the organic phase in the cooling medium when it is fed into the cooling zones prior to the contacting with the product gas stream being from 0.015:1 to 10:1, Cb) compressing the cooled product gas stream b which may have been depleted of high-boiling secondary components in at least one compression stage, giving at least one aqueous condensate stream c1 and one gas stream c2 comprising butadiene, n-butenes, water vapor, oxygen and low-boiling hydrocarbons, with or without carbon oxides and with or without inert gases;

D) removing uncondensable and low-boiling gas constituents comprising oxygen and low-boiling hydrocarbons, with or without carbon oxides and with or without inert gases, as gas stream d2 from the gas stream c2 by absorbing the $C_4$ hydrocarbons comprising butadiene and n-butenes in an absorbent, giving an absorbent stream laden with $C_4$ hydrocarbons and the gas stream d2, and then desorbing the $C_4$ hydrocarbons from the laden absorbent stream, giving a $C_4$ product gas stream d1, E) separating the $C_4$ product stream d1 by extractive distillation with a butadiene-selective solvent into a stream e1 comprising butadiene and the selective solvent and a stream e2 comprising n-butenes;

F) distilling the stream e1 comprising butadiene and the selective solvent into a stream f1 consisting essentially of the selective solvent and a stream f2 comprising butadiene.

16 Claims, 4 Drawing Sheets

(51) Int. Cl.
 *C07C 7/08* (2006.01)
 *C07C 7/11* (2006.01)
 *C07C 7/09* (2006.01)

(58) Field of Classification Search
 CPC ...... C07C 2523/887; C10G 2300/1081; C10G 2300/1092; C10G 2400/20; C10G 27/00; C10G 27/04
 See application file for complete search history.

(56) References Cited

U.S. PATENT DOCUMENTS

| | | | |
|---|---|---|---|
| 3,956,181 A | 5/1976 | Grasselli et al. | |
| 4,162,234 A | 7/1979 | Grasselli et al. | |
| 4,336,409 A | 6/1982 | Yamamoto et al. | |
| 4,397,771 A | 8/1983 | Grasselli et al. | |
| 4,423,281 A | 12/1983 | Yamamoto et al. | |
| 4,424,141 A | 1/1984 | Grasselli et al. | |
| 4,547,615 A | 10/1985 | Yamamoto | |
| 7,482,500 B2 * | 1/2009 | Johann | C07C 5/333 585/325 |
| 9,255,041 B2 | 2/2016 | Yano et al. | |
| 2012/0130137 A1 | 5/2012 | Orita et al. | |
| 2014/0200381 A1 * | 7/2014 | Josch | C07C 7/05 585/621 |

FOREIGN PATENT DOCUMENTS

| | | |
|---|---|---|
| DE | 2530959 A1 | 2/1976 |
| DE | 2600128 A1 | 7/1976 |
| JP | 2011001341 A | 1/2011 |
| JP | 2011006381 A | 1/2011 |
| JP | 2013119530 A | 6/2013 |
| JP | 2013177380 A | 9/2013 |
| KR | 20130036467 A | 4/2013 |
| KR | 20130036468 A | 4/2013 |
| WO | WO-2012157495 A1 | 11/2012 |
| WO | WO-2014111406 A1 | 7/2014 |

OTHER PUBLICATIONS

Written Opinion of the International Searching Authority for PCT/EP2015/068436 dated Oct. 16, 2015.

\* cited by examiner

PROCESS FOR PREPARING 1,3-BUTADIENE FROM N-BUTENES BY OXIDATIVE DEHYDROGENATION

CROSS-REFERENCE TO RELATED APPLICATIONS

This application is a national stage application (under 35 U.S.C. § 371) of PCT/EP2015/068436, filed Aug. 11, 2015, which claims benefit of European Application No. 14180700.8, filed Aug. 12, 2014, both of which are incorporated herein by reference in their entirety.

The invention relates to a process for preparing 1,3-butadiene (butadiene) from n-butenes by oxidative dehydrogenation (ODH).

Butadiene is an important base chemical and is used, for example, for production of synthetic rubbers (butadiene homopolymers, styrene-butadiene rubber or nitrile rubber) or for production of thermoplastic terpolymers (acrylonitrile-butadiene-styrene copolymers). Butadiene is also converted to sulfolane, chloroprene and 1,4-hexamethylenediamine (via 1,4-dichlorobutene and adiponitrile). Through dimerization of butadiene, it is also possible to obtain vinylcyclohexene, which can be dehydrogenated to styrene.

Butadiene can be prepared by thermal cracking (steam-cracking) of saturated hydrocarbons, typically proceeding from naphtha as the raw material. The steamcracking of naphtha affords a hydrocarbon mixture of methane, ethane, ethene, acetylene, propane, propene, propyne, allene, butanes, butenes, 1,3-butadiene and 1,2-butadiene, butynes, methylallene, and $C_5$ and higher hydrocarbons.

Butadiene can also be obtained by the oxidative dehydrogenation of n-butenes (1-butene and/or 2-butene). The input gas utilized for the oxidative dehydrogenation (oxydehydrogenation, ODH) of n-butenes to butadiene may be any desired mixture comprising n-butenes. For example, it is possible to use a fraction which comprises n-butenes (1-butene and/or 2-butene) as the main constituent and has been obtained from the $C_4$ fraction from a naphtha cracker by removing butadiene and isobutene. In addition, it is also possible to use gas mixtures which comprise 1-butene, cis-2-butene, trans-2-butene or mixtures thereof and have been obtained by dimerization of ethylene as input gas. In addition, input gases used may be gas mixtures which comprise n-butenes and have been obtained by catalytic fluidized bed cracking (fluid catalytic cracking, FCC).

Processes for oxidative dehydrogenation of butenes to butadiene are known in principle US 2012/0130137 A1, for example, describes a process of this kind using catalysts comprising oxides of molybdenum, bismuth and generally further metals. For the lasting activity of such catalysts for the oxidative dehydrogenation, a critical minimum level of partial oxygen pressure is required in the gas atmosphere in order to avoid an excessive reduction and hence a loss of performance of the catalysts. For this reason, it is generally also not possible to work with a stoichiometric oxygen input or complete oxygen conversion in the oxydehydrogenation reactor (ODH reactor). US 2012/0130137 describes, for example, an oxygen content of 2.5% to 8% by volume in the starting gas.

The need for an oxygen excess for such catalyst systems is common knowledge and is reflected in the process conditions when catalysts of this kind are used. Representative examples include the comparatively recent studies by Jung et al. (Catal. Surv. Asia 2009, 13, 78-93; DOI 10.1007/s10563-009-9069-5 and Applied Catalysis A: General 2007, 317, 244-249; DOI 10.1016/j.apcata.2006.10.021).

JP-A 2011-006381 to Mitsubishi addresses the risk of peroxide formation in the workup section of a process for preparing conjugated alkadienes. As a solution, the addition of polymerization inhibitors to the absorption solutions for the process gases and the setting of a maximum peroxide content of 100 ppm by weight by heating the absorption solutions is described. However, there is no information as to avoidance or monitoring of peroxides in upstream process steps. A particularly critical aspect is the step of cooling the ODH reactor output with a water quench. Organic peroxides formed are barely soluble in water, and so they are deposited and can accumulate in the apparatus in solid or liquid form, instead of being discharged with the aqueous purge stream. At the same time, the temperature of the water quench is not so high that sufficiently high and constant breakdown of the peroxides formed can be assumed The catalytic oxidative dehydrogenation can form high-boiling secondary components, for example maleic anhydride, phthalic anhydride, benzaldehyde, benzoic acid, ethylbenzene, styrene, fluorenone, anthraquinone and others. Deposits of these components can lead to blockages and to a rise in the pressure drop in the reactor or beyond the reactor in the workup area, and can thus disrupt regulated operation. Deposits of the high-boiling secondary components mentioned can also impair the function of heat exchangers or damage moving apparatuses such as compressors. Steam-volatile compounds such as fluorenone can get through a quench apparatus operated with water and precipitate beyond it in the gas discharge lines. In principle, there is therefore also the risk that solid deposits will get into downstream apparatus parts, for example compressors, and cause damage there.

US 2012/0130137 A1 paragraph [0122] also refers to the problem of high-boiling by-products. Particular mention is made of phthalic anhydride, anthraquinone and fluorenone, which are said to be present typically in concentrations of 0.001% to 0.10% by volume in the product gas. US 2012/0130137 A1 paragraphs [0124]-[0126] recommends cooling the hot reactor discharge gases directly, by contact with a cooling liquid (quench tower), at first to typically 5 to 100° C. The cooling liquids mentioned are water or aqueous alkali solutions. There is explicit mention of the problem of blockages in the quench by high boilers from the product gas or by polymerization products of high-boiling by-products from the product gas, and for this reason it is said to be advantageous that high-boiling by-products are entrained as little as possible from the reaction section to the cooling section (quench).

JP-A 2011-001341 describes a two-stage cooling operation for a process for oxidative dehydrogenation of alkenes to conjugated alkadienes. This involves first cooling the product discharge gas from the oxidative dehydrogenation to a temperature between 300 and 221° C. and then cooling it further to a temperature between 99 and 21° C. Paragraphs [0066] ff. state that the temperature between 300 and 221° C. is preferably established using heat exchangers, but a portion of the high boilers could also precipitate out of the product gas in these heat exchangers. JP-A 2011-001341 therefore describes occasional washing of deposits out of the heat exchangers with organic or aqueous solvents. Solvents described are, for example, aromatic hydrocarbons such as toluene or xylene, or an alkaline aqueous solvent, for example the aqueous solution of sodium hydroxide. In order to avoid excessive frequency of interruption of the process to clean the heat exchanger, JP-A 2011-001341 describes a setup having two heat exchangers arranged in parallel, which are each alternately operated or rinsed (called A/B operation mode).

JP-A 2013-119530 describes a quench in which an ODH product gas is cooled by direct contact with water. Paragraph 7 addresses the problem that the product gas entrains solid constituents and that these can prevent stable operation. Solid constituents were even said to be found in the offgas of the quench column. Paragraph 41 asserts that these constituents consist mainly of isophthalic acid and terephthalic acid. Even if the amount in the offgas is small, it is said that filters, for example, could be covered very rapidly. According to this application, the solid constituents are eliminated as far as possible from the product gas through suitable choice of internals and of the volume flow ratio of coolant and gas stream. However, the application does not give any information as to how blockage of the coolant circuit can be avoided.

JP-A 2013-177380 describes, in paragraph 60, possible coolants used in the product gas quench. Cooling liquids mentioned in general terms saturated hydrocarbons, unsaturated hydrocarbons, aromatic hydrocarbons, esters, ethers, aldehydes, ketones, amines, acids, water and mixtures thereof. The preferred coolant is water. Paragraph 62 describes the supply and removal of water as coolant: according to this, at least a portion of the water which has been discharged from the bottom of the cooling tower can be fed back to a middle stage and/or to the top of the cooling tower. The water withdrawn from the bottom may comprise solids. For the removal thereof, the document suggests standard processes, for example the use of a screen. Paragraphs 63 and 64 mention, as by-products which condense out in the coolant, oxygenous organic compounds such as aldehydes, ketones, carboxylic acid, unsaturated aldehydes, unsaturated carboxylic acid, and polymers having the compounds mentioned as a structural unit. The document does not make any statement as to how stable circulation of the coolant can be assured in spite of the solids content.

According to WO 2012/157495, the aqueous solution of an organic amine is used as coolant in the product gas quench of an oxydehydrogenation. Paragraph 6 describes the problem of blockage of lines by solids. Accordingly, it has been found that high-boiling by-products such as organic acids, aldehydes and ketones condense when the reaction product gas is quenched with cooling water and flow along with the flow of the reaction product gas, which results in blockage of lines and endangerment of the continuous operation of the plant.

Effective removal of the components is said to be achieved through use of an aqueous solution of an organic amine and of a preferably aromatic solvent. However, the two coolants are used in separate regions of the cooling tower. Thus, paragraph 35 states that a first quench tower is used for the scrubbing of the reaction product gas with the aqueous solution of organic amine, and a second quench tower for the purification of the reaction product gas with the aromatic solvent.

KR 2013-0036467 and KR 2013-0036468 describe the use of a mixture of water and a water-miscible organic solvent as coolant in a product gas quench of an oxydehydrogenation. Owing to water miscibility, the workup and regeneration of the organic solvent is very energy-intensive and is disadvantageous from an economic point of view.

It is an object of the present invention to provide a process which remedies the abovementioned disadvantages of known processes. More particularly, a process in which deposits resulting from high-boiling organic secondary constituents in the apparatuses connected downstream of the ODH are avoided is to be provided. In addition, a process in which the possible accumulation of organic peroxides is avoided is to be provided. More particularly, a process in which there are no blockages by solids dispersed in the coolant in the coolant circuit (quench circuit), especially in the nozzles through which the coolant is fed into the cooling zone, and stable continuous quench circulation is assured, is to be provided.

The object is achieved by a process for preparing butadiene from n-butenes, comprising the steps of:

A) providing an input gas stream a comprising n-butenes,

B) feeding the input gas stream a comprising n-butenes and at least one oxygenous gas into at least one oxidative dehydrogenation zone and oxidatively dehydrogenating n-butenes to butadiene, giving a product gas stream b comprising butadiene, unconverted n-butenes, water vapor, oxygen, low-boiling hydrocarbons and high-boiling secondary components, with or without carbon oxides and with or without inert gases;

Ca) cooling the product gas stream b by contacting with a cooling medium in at least one cooling zone, the cooling medium being at least partly recycled and having an aqueous phase and an organic phase, and the mass ratio of the aqueous phase to the organic phase in the cooling medium when it is fed into the cooling zones prior to the contacting with the product gas stream being from 0.13:1 to 100:1;

Cb) compressing the cooled product gas stream b which may have been depleted of high-boiling secondary components in at least one compression stage, giving at least one aqueous condensate stream c1 and one gas stream c2 comprising butadiene, n-butenes, water vapor, oxygen and low-boiling hydrocarbons, with or without carbon oxides and with or without inert gases;

D) removing uncondensable and low-boiling gas constituents comprising oxygen and low-boiling hydrocarbons, with or without carbon oxides and with or without inert gases, as gas stream d2 from the gas stream c2 by absorbing the $C_4$ hydrocarbons comprising butadiene and n-butenes in an absorbent, giving an absorbent stream laden with $C_4$ hydrocarbons and the gas stream d2, and then desorbing the $C_4$ hydrocarbons from the laden absorbent stream, giving a $C_4$ product gas stream d1;

E) separating the $C_4$ product stream d1 by extractive distillation with a butadiene-selective solvent into a stream e1 comprising butadiene and the selective solvent and a stream e2 comprising n-butenes;

F) distilling the stream e1 comprising butadiene and the selective solvent into a stream f1 consisting essentially of the selective solvent and a stream f2 comprising butadiene.

The object is also achieved by an apparatus for performing this process, having the following components:

I) a reactor for oxidative dehydrogenation of n-butenes to butadiene, having at least one inlet for feeding in an input gas stream comprising n-butenes and a gas containing at least oxygen, and having at least one outlet for a product gas stream comprising butadiene, unconverted n-butenes, water vapor, oxygen, low-boiling hydrocarbons and high-boiling secondary components, with or without carbon oxides and with or without inert gases;

II) units having a coolant circuit for cooling the product gas stream by contacting with a cooling medium, the cooling medium being at least partly recyclable;

III) unit for compression of the cooled product gas stream, comprising at least one compression stage;

IV) unit for removing uncondensable and low-boiling gas constituents from a $C_4$ hydrocarbon stream, comprising an absorbent for $C_4$ hydrocarbons comprising butadiene and n-butenes;

V) unit for desorbing $C_4$ hydrocarbons from the absorbent stream laden with the $C_4$ hydrocarbons;

VI) unit for separating $C_4$ hydrocarbons comprising butadiene and n-butenes by extractive distillation, comprising a butadiene-selective solvent;

VII) unit for distilling a stream comprising the butadiene and the selective solvent.

Figure 1:
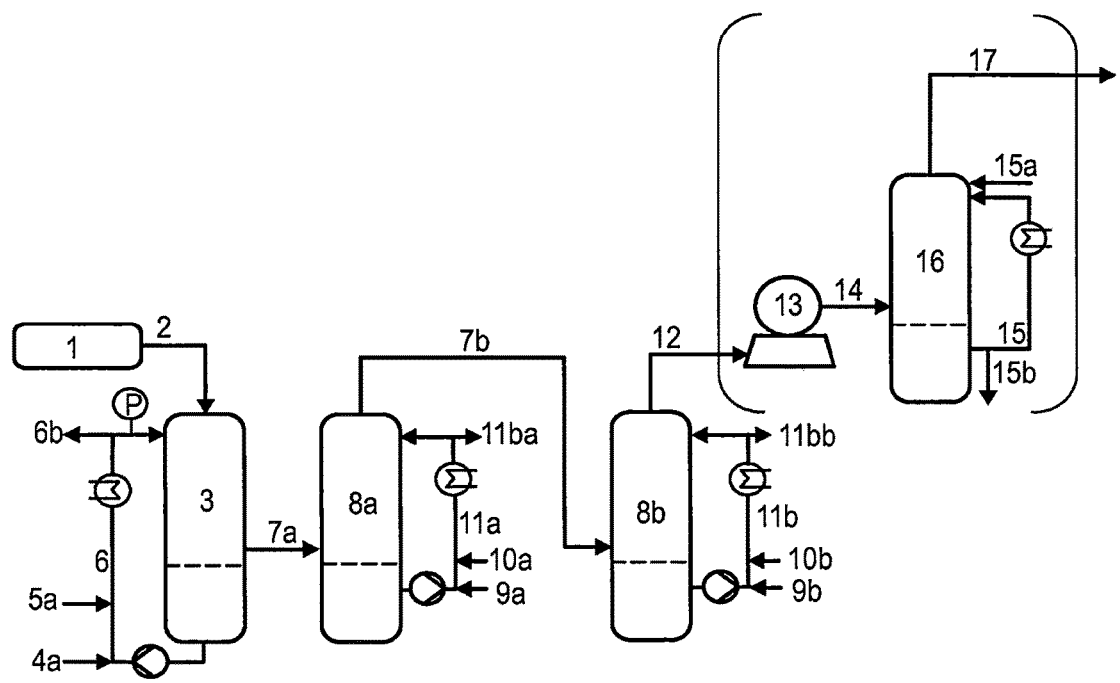
FIGS. 1-4 illustrate embodiments according to the invention

It has been found that continuous operation of the quench circuit is possible for longer when the circuit is operated with two mutually immiscible coolants. In addition, continuous operation is possible for a particularly long period when the two immiscible solvents are in a particular ratio on entry into the quench column. In addition, continuous operation is possible for a particularly long period when the two immiscible solvents are dispersed intimately with one another on entry into the quench column.

According to the invention, in the cooling stage Ca), a biphasic dispersion of one or more organic solvents and an aqueous phase is used. The rapid cooling of the product gas stream in the quench results in condensation of high-boiling secondary components. Organic solvents generally have a very much higher dissolution capacity for the high-boiling by-products which can lead to deposits and blockages in the plant parts downstream of the ODH reactor than water or aqueous alkaline solutions. Organic solvents used according to the invention are aromatic hydrocarbons, more preferably toluene, o-xylene, m-xylene, p-xylene, mesitylene, mono-, di- and triethylbenzene, mono-, di- and triisopropylbenzene and mixtures thereof. A very preferably used solvent is mesitylene. Generally these solvents are present in a purity of at least 90% by weight.

On a technical scale, organic solvents are frequently not available as pure substances. An organic solvent normally has a purity of at least 90% by weight, preferably at least 94% by weight and more preferably at least 96% by weight. Technical mesitylene, for example, contains in general at least 90% by weight of pure mesitylene, preferably at least 94% by weight mesitylene and more preferably at least 96% by weight mesitylene. Typical impurities comprise other isomers of trimethylbenzene, isomers of dimethylbenzene, and monomethylbenzene, mono-, di- and triisopropylbenzene, but also small amounts of further aromatic, in particular alkylaromatic compounds.Likewise, small amounts of aliphatic side components can be contained.

It has additionally been found that the presence of an additional aqueous phase in the circulating cooling medium can result in effective avoidance of blockages in the quench circuit, especially in the region of the nozzles through which the coolant enters the quench column, but also, for example, in the pumps of the coolant circuit and in analytical instruments which measure the volume flow rate of the circulation. This is attributed to the fact that the condensed high-boiling secondary components also include substances which have only a low solubility in an organic solvent but have significantly better solubility in water or aqueous solutions. The effect of this is that tackifying substances are dissolved in the organic and aqueous phase, the result of which is that coke-like insoluble solids remain dispersed in the coolant circuit, and are not deposited on plant parts such as nozzles and do not lead to blockages therein.

The phase ratio, i.e. the ratio of the mass of the aqueous phase to the mass of the organic phase of the cooling medium on entry into the cooling stage (quench stage) prior to contacting is determined via the flow rates of the aqueous and organic coolants added to the coolant circuit, the flow rate of water vapor present in the product gas stream, the flow rates of water vapor and organic coolant which leave the cooling stage, and the flow rates of the aqueous and organic phases which are withdrawn from the coolant circuit as output stream (purge). The phase ratio is greater than or equal to 0.13:1, preferably greater than or equal to 0.15:1, more preferably greater than or equal to 0.18:1, and very preferably greater than or equal to 0.2:1 and especially greater than or equal 0.3:1, and less than or equal to 100:1, preferably less than or equal to 10:1, more preferably less than or equal to 2:1, especially less than or equal to 1:1. Preferred ranges for the phase ratio are from 0.15:1 to 10:1, in particular from 0.18:1 to 2:1.

Preferably, the cooling medium on entry into the cooling zone has very good dispersion of the two phases. A basic measure used for the dispersion quality is a relative standard deviation $\sigma/\sigma 0$. See, for example, Kraume et al., "Continuous Mixing of Fluids" in Ullmann's Encyclopedia of Industrial Chemistry, Wiley-VCH (2012); or Streiff, Chem, Ing. Tech. 52, 520 (1980). The test method used is the conductivity test method according to Phal and Muschelknautz, Chem. Ing. Tech. 51, 347 (1979). In this method, the different electrical conductivities of aqueous and organic phase are exploited, and the electrical conductivity and hence the concentration of the two phases are measured with spatial resolution. An ideal dispersion would thus exist at $\sigma/\sigma 0=0$. Preferably, the components forming the organic phase and the components forming the aqueous phase in the biphasic cooling medium have a coefficient of variation of less than 1, preferably of less than 0.5, more preferably of less than 0.1.

A high degree of dispersion of the cooling medium can be effected, for example, through the incorporation of suitable mixers into the circuit. The type of mixer is not restricted any further here, and comprises stirrers, static mixers and restrictors.

In addition, a high degree of dispersion of the cooling medium can be achieved by means of a nozzle. For the Reynolds number Re of a flow generated in a nozzle, the following expression is adopted for each of the two phases of the coolant:

$Re = (\rho \times v \times d)/\eta$ with $\rho$=density of the respective phase
$v$=flow rate of the respective phase
$d$=length (nozzle opening here)
$\eta$=dynamic viscosity of the respective phase For water having a circulation flow rate of 60 l/h, a nozzle opening of 1.15 mm and a dynamic viscosity of water at 20° C. of $10^{-3}$ Pa s, this gives, for example:

$v$=volume flow rate/area=1.66 $10^{-5}/(pi*(1.15/2\ 10^{-3})^2)$=16 m/s $Re=(1000\ kg/m^3 \times 16\ m/s \times 1.15\ 10^{-3}\ m)/10^{-3}$ Pa s=18 400.

In general, the Reynolds number Re of the two phases of the cooling medium on entry into the cooling stage is greater than 100, preferably greater than 500 and more preferably greater than 1000.

A further crucial factor for a high degree of dispersion is a high volume-specific power input into the cooling medium. This can in turn be achieved, for example, by means of suitable mixers, pumps or nozzles.

The volume-specific power input $P_v$ is assumed to be:

$$P_v = \Delta p \dot{V}/(V)$$

with $\Delta p$=pressure drop over the power-introducing process unit
$\dot{V}$=circulation volume flow rate of the coolant
v=specific volume of the process unit For a cooling medium having a circulation volume flow rate of 60 l/h, a pressure drop over the nozzle of 500 mbar and a nozzle volume of 0.1 cm$^3$, for example, this gives:

$$P_v = 500\ \text{mbar} \times 60\ \text{l/h}/10\ \text{mm}^3 = 5\ 10^4 (\text{kg/ms}^2) \times 1.6\ 10^{-5}(\text{m}^3/\text{s})/10^{-7}\ \text{m}^3 = 8\ 10^7\ \text{W/m}^3.$$

In general, the volume-specific power input into the coolant in circulation is at least $10^3$ W/m$^3$, preferably at least $10^4$ W/m$^3$, and more preferably at least $10^5$ W/m$^3$.

In general, the cooling medium is fed into the cooling zone(s) through one or more nozzles. In a preferred embodiment, a flow with a Reynolds number Re of at least 1000 is produced here in the nozzle(s). The power input here is at least $10^3$ W/m$^3$. More particularly, this achieves such good dispersion of the two phases that the coefficient of variation for each component of each phase of the cooling medium on entry into the cooling zones is less than 1.

Embodiments which follow are preferred or particularly preferred variants of the process according to the invention:

Stage Ca) is performed in multiple stages in stages Ca1) to Can), preferably Ca1) and Ca2). In this case, at least a portion of the cooling medium may be fed as coolant to the first stage Ca1) after it has passed through the second stage Ca2).

Stage Cb) generally comprises at least one compression stage Cba) and at least one cooling stage Cbb). Preferably, in the at least one cooling stage Cbb), the gas compressed in the compression stage Cba) is contacted with a coolant. More preferably, the coolant in the cooling stage Cbb) comprises the same organic solvent which is used as a coolant in stage Ca). In an especially preferred variant, at least some of this coolant is fed as a coolant to stage Ca) after it has passed through the at least one cooling stage Cbb).

Preferably, stage Cb) comprises a plurality of compression stages Cba1) to Cban) and cooling stages Cbb1) to Cbbn), for example four compression stages Cba1) to Cba4) and four cooling stages Cbb1) to Cbb4).

Preferably, step D) comprises steps Da) to Dc):
Da) absorbing the C$_4$ hydrocarbons comprising butadiene and n-butenes in a high-boiling absorbent, giving an absorbent stream laden with C$_4$ hydrocarbons and the gas stream d2,
Db) removing oxygen from the absorbent stream laden with C$_4$ hydrocarbons from step Da) by stripping with an uncondensable gas stream, and
Dc) desorbing the C$_4$ hydrocarbons from the laden absorbent stream, giving a C$_4$ product gas stream d1 consisting essentially of C$_4$ hydrocarbons and comprising less than 100 ppm of oxygen.

Preferably, the high-boiling absorbent used in step Da) is an aromatic hydrocarbon solvent, more preferably the aromatic hydrocarbon solvent used in step Ca), especially toluene, o-xylene, m-xylene, p-xylene, mesitylene or mixtures thereof.

In a step A), an input gas stream comprising n-butenes is provided.

Input gas streams used may be pure n-butenes (1-butene and/or cis/trans-2-butene), but also gas mixtures comprising butenes. Such a gas mixture can be obtained, for example, by nonoxidative dehydrogenation of n-butane. It is also possible to use a fraction which comprises n-butenes (1-butene and cis/trans-2-butene) as the main constituent and has been obtained from the C$_4$ fraction from naphtha cracking by removal of butadiene and isobutene. In addition, it is also possible to use, as input gas, gas mixtures which comprise pure 1-butene, cis-2-butene, trans-2-butene or mixtures thereof, and which have been obtained by dimerization of ethylene. In addition, input gases used may be gas mixtures which comprise n-butenes and have been obtained by catalytic fluidized bed cracking (fluid catalytic cracking, FCC).

In one embodiment of the process according to the invention, the input gas comprising n-butenes is obtained by nonoxidative dehydrogenation of n-butane. Through the coupling of a nonoxidative catalytic dehydrogenation with the oxidative dehydrogenation of the n-butenes formed, it is possible to obtain a high yield of butadiene, based on n-butane used. The nonoxidative catalytic n-butane dehydrogenation gives a gas mixture which, as well as butadiene, 1-butene, 2-butenes and unconverted n-butane, comprises secondary constituents. Typical secondary constituents are hydrogen, water vapor, nitrogen, CO and CO$_2$, methane, ethane, ethene, ropane and propene. The composition of the gas mixture leaving the first dehydrogenation zone may vary significantly depending on the mode of operation of the dehydrogenation. For instance, in the case of performance of the dehydrogenation while feeding in oxygen and additional hydrogen, the product gas mixture has a comparatively high content of water vapor and carbon oxides. In the case of modes of operation without feeding of oxygen, the product gas mixture of the nonoxidative dehydrogenation has a comparatively high content of hydrogen.

In step B) the input gas stream comprising n-butenes and at least one oxygenous gas are fed into at least one dehydrogenation zone and the butenes present in the gas mixture are oxidatively dehydrogenated to butadiene in the presence of an oxydehydrogenation catalyst.

Catalysts suitable for the oxydehydrogenation are generally based on an Mo—Bi—O-containing multimetal oxide system which generally additionally comprises iron. In general, the catalyst system also comprises further additional components, for example potassium, cesium, magnesium, zirconium, chromium, nickel, cobalt, cadmium, tin, lead, germanium, lanthanum, manganese, tungsten, phosphorus, cerium, aluminum or silicon. Iron-containing ferrites have also been proposed as catalysts.

In a preferred embodiment, the multimetal oxide comprises cobalt and/or nickel. In a further preferred embodiment, the multimetal oxide comprises chromium. In a further preferred embodiment, the multimetal oxide comprises manganese.

Examples of Mo—Bi—Fe—O-containing multimetal oxides are Mo—Bi—Fe—Cr—O— or Mo—Bi—Fe—Zr—O— containing multimetal oxides. Preferred systems are described, for example, in U.S. Pat. No. 4,547,615 (Mo$_{12}$BiFe$_{0.1}$Ni$_8$ZrCr$_3$K$_{0.2}$O$_x$ and Mo$_{12}$BiFe$_{0.1}$Ni$_8$AlCr$_3$K$_{0.2}$O$_x$), U.S. Pat. No. 4,424,141 (Mo$_{12}$BiFe$_3$Co$_{4.5}$Ni$_{2.5}$P$_{0.5}$K$_{0.1}$O$_x$+SiO$_2$), DE-A 25 30 959 (Mo$_{12}$BiFe$_3$Co$_{4.5}$Ni$_{2.5}$Cr$_{0.5}$K$_{0.1}$O$_x$, Mo$_{13.75}$BiFe$_3$Co$_{4.5}$Ni$_{2.5}$Ge$_{0.5}$K$_{0.8}$O$_x$, Mo$_{12}$BiFe$_3$Co$_{4.5}$Ni$_{2.5}$Mn$_{0.5}$K$_{0.1}$O$_x$ and Mo$_{12}$BiFe$_3$Co$_{4.5}$Ni$_{2.5}$La$_{0.5}$K$_{0.1}$O$_x$), U.S. Pat. No. 3,911,039

($Mo_{12}BiFe_3Co_{4.5}Ni_{2.5}Sn_{0.5}K_{0.1}O_x$), DE-A 25 30 959 and DE-A 24 47 825 ($Mo_{12}BiFe_3Co_{4.5}Ni_{2.5}W_{0.5}K_{0.1}O_x$).

Suitable multimetal oxides and the preparation thereof are additionally described in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_3Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

Particularly preferred catalytically active multimetal oxides comprising molybdenum and at least one further metal have the general formula (Ia):

$$Mo_{12}Bi_aFe_bCo_cNi_dCr_eX^1_fX^2_gO_y \qquad (Ia)$$

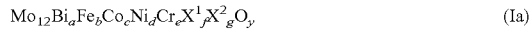

with

Xi=Si, Mn and/or Al, $X^2$=Li, Na, K, Cs and/or Rb, 0.2≤a≤1, 0.5≤b≤10,

0≤c≤10,

0≤d≤10,

2≤c+d≤10

0≤e≤2, 0 f≤10,

0≤g≤0.5, y=a number which, with the prerequisite of charge neutrality, is determined by the valency and frequency of the elements in (Ia) other than oxygen.

Preference is given to catalysts whose catalytically active oxide composition, of the two metals Co and Ni, has only Co (d=0). Preferred is $X^1$ Si and/or Mn and $X^2$ is preferably K, Na and/or Cs, more preferably $X^2$=K.

The molecular oxygen-comprising gas comprises generally more than 10% by volume, preferably more than 15% by volume and even more preferably more than 20% by volume of molecular oxygen. It is preferably air. The upper limit for the content of molecular oxygen is generally 50% by volume or less, preferably 30% by volume or less and even more preferably 25% by volume or less. In addition, any desired inert gases may be present in the molecular oxygen-comprising gas. Possible inert gases may include nitrogen, argon, neon, helium, CO, $CO_2$ and water. The amount of inert gases, for nitrogen, is generally 90% by volume or less, preferably 85% by volume or less and even more preferably 80% by volume or less. In the case of constituents other than nitrogen, it is generally 10% by volume or less, preferably 1% by volume or less.

For performance of the oxidative dehydrogenation at full conversion of n-butenes, preference is given to a gas mixture having a molar oxygen:n-butenes ratio of at least 0.5. Preference is given to working at an oxygen:n-butenes ratio of 0.55 to 10. To set this value, the input gas can be mixed with oxygen or one or more oxygenous gases, for example air, and optionally additional inert gas or water vapor. The oxygenous gas mixture obtained is then fed to the oxydehydrogenation.

The reaction temperature in the oxydehydrogenation is generally controlled by a heat exchange medium present around the reaction tubes. Examples of useful liquid heat exchange media of this kind include melts of salts such as potassium nitrate, potassium nitrite, sodium nitrite and/or sodium nitrate, and melts of metals such as sodium, mercury and alloys of various metals. It is also possible to use ionic liquids or heat carrier oils. The temperature of the heat exchange medium is between 220 to 490° C., preferably between 300 to 450° C. and more preferably between 350 and 420° C.

Because of the exothermicity of the reactions which proceed, the temperature in particular sections of the reaction interior during the reaction may be higher than that of the heat exchange medium, and what is called a hotspot develops. The position and magnitude of the hotspot is decided by the reaction conditions, but it can also be regulated through the dilution ratio of the catalyst layer or the flow rate of mixed gas. The difference between hotspot temperature and the temperature of the heat exchange medium is generally between 1 to 150° C., preferably between 10 to 100° C. and more preferably between 20 to 80° C. The temperature at the end of the catalyst bed is generally between 0 to 100° C., preferably between 0.1 to 50° C., more preferably between 1 to 25° C., above the temperature of the heat exchange medium.

The oxydehydrogenation can be performed in all fixed bed reactors known from the prior art, for example in a staged oven, in a fixed bed tubular reactor or shell and tube reactor, or in a plate heat exchanger reactor. A shell and tube reactor is preferred.

Preferably, the oxidative dehydrogenation is performed in fixed bed tubular reactors or fixed bed shell and tube reactors. The reaction tubes (just like the other elements of the shell and tube reactor) are generally manufactured from steel. The wall thickness of the reaction tubes is typically 1 to 3 mm. The internal diameter thereof is generally (uniformly) 10 to 50 mm or 15 to 40 mm, frequently 20 to 30 mm. The number of reaction tubes accommodated in a shell and tube reactor generally runs to at least 1000, or 3000, or 5000, preferably to at least 10 000. Frequently, the number of reaction tubes accommodated in a shell and tube reactor is 15 000 to 30 000, or to 40 000 or to 50 000. The length of the reaction tubes normally extends to a few meters, a typical reaction tube length being in the range from 1 to 8 m, frequently 2 to 7 m, in many cases 2.5 to 6 m.

The invention is elucidated in detail hereinafter with reference to FIGS. 1 to 4.

The catalyst bed installed in the ODH reactor 1 may consist of a single layer or of 2 or a sequence of variable layers (called a structured bed), These layers may consist of a pure catalyst or be diluted with a material which does not react with the input gas or components from the product gas of the reaction. In addition, the catalyst layers may consist of shaped bodies of unsupported material or supported eggshell catalysts.

The product gas stream 2 leaving the oxidative dehydrogenation comprises, as well as butadiene, generally also unconverted 1-butene and 2-butene, oxygen and water vapor. As secondary components, it generally further comprises carbon monoxide, carbon dioxide, inert gases (principally nitrogen), low-boiling hydrocarbons such as methane, ethane, ethene, propane and propene, butane and isobutane, with or without hydrogen and with or without oxygen-containing hydrocarbons, called oxygenates. Oxygenates may, for example, be formaldehyde, furan, acetaldehyde, acetic acid, maleic anhydride, formic acid, methacrolein, acrolein, propionaldehyde, methacrylic acid, crotonaldehyde, crotonic acid, propionic acid, acrylic acid, methyl vinyl ketone, styrene, benzaldehyde, benzoic acid, phthalic anhydride, fluorenone, anthraquinone and butyraldehyde.

The product gas stream 2 at the reactor outlet is characterized by a temperature close to the temperature at the end of the catalyst bed. The product gas stream is then brought to a temperature of 150 to 400° C., preferably 160 to 300° C., more preferably 170 to 250° C. It is possible to insulate the line through which the product gas stream flows, or to use a heat exchanger, in order to keep the temperature within the desired range. Any heat exchanger system is possible, provided that this system can be used to keep the temperature of the product gas at the desired level. Examples of a heat exchanger include spiral heat exchangers, plate heat exchangers, double tube heat exchangers, multitube heat exchangers, boiler-spiral heat exchangers, boiler-shell heat exchangers, liquid-liquid contact heat exchangers, air heat exchangers, direct contact heat exchangers and fin tube heat exchangers. Since, while the temperature of the product gas is set to the desired temperature, some of the high-boiling by-products present in the product gas can precipitate out, the heat exchanger system should therefore preferably have two or more heat exchangers. If two or more heat exchangers provided are arranged in parallel in this case, and distributed cooling of the product gas obtained in the heat exchangers is thus enabled, the amount of high-boiling by-products which are deposited in the heat exchangers decreases, and hence the service life thereof can be extended. As an alternative to the abovementioned method, the two or more heat exchangers provided may be arranged in parallel. The product gas is supplied to one or more, but not to all, heat exchangers, which are succeeded by other heat exchangers after a certain operation period. In the case of this method, the cooling can be continued, some of the heat of reaction can be recovered and, in parallel, the high-boiling by-products deposited in one of the heat exchangers can be removed. It is possible to use a solvent as an abovementioned organic solvent, provided that it is capable of dissolving the high-boiling by-products. Examples are aromatic hydrocarbon solvents, for example toluene and xylenes and mesitylene, and alkaline aqueous solvent, for example the aqueous solution of sodium hydroxide.

Subsequently, a majority of the high-boiling secondary components and of the water is removed from the product gas stream 2 by cooling and compression. According to the invention, the cooling is effected by contacting with a biphasic cooling medium comprising an aqueous phase and an organic phase. This stage is also referred to hereinafter as the quench. This quench may consist of only one stage (3 in FIGS. 1 to 3) or of a plurality of stages (for example 3, 8 in FIGS. 1 to 3). Product gas stream 2 is thus contacted directly with a biphasic cooling medium 6 and hence cooled. The organic phase comprises organic solvents, preferably aromatic hydrocarbons, more preferably toluene, o-xylene, m-xylene, p-xylene, mesitylene, all the possible constitutional isomers of mono-, di- and triethylbenzene, or mixtures thereof, used. Preference is also given to aromatic hydrocarbons having a boiling point at 1013.25 hPa of more than 120° C., or mixtures thereof.

In general, product gas 2, according to the presence and temperature level of any heat exchanger upstream of the quench 3, has a temperature of 100 to 440° C. The product gas is contacted in the quench stage 3 with the cooling medium composed of aqueous and organic phase. In this operation, the cooling medium is introduced preferably through a nozzle, in order to achieve very efficient mixing of the aqueous and organic phases on the one hand, and of the biphasic cooling medium with the product gas on the other hand. For the same purpose, it is possible to introduce internals, for example further nozzles, in the quench stage, through which the product gas and the cooling medium pass together. The coolant inlet into the quench is designed such that blockage by deposits in the region of the coolant inlet is minimized.

In general, product gas 2 is cooled in the first quench stage 3 to 5 to 180° C., preferably to 30 to 130° C. and even more preferably to 50 to 110° C. The temperature of the cooling medium 6 at the inlet may generally be 5 to 200° C., preferably 20 to 120° C., especially preferably 30 to 90° C. The pressure in the first quench stage 3 is not particularly restricted, but is generally 0.01 to 5 bar (g), preferably 0.1 to 2 bar (g) and more preferably 0.2 to 3 bar (g). If any great amounts of high-boiling by-products are present in the product gas, high-boiling by-products may readily polymerize and result in deposits of solids which are caused by high-boiling by-products in this process section. In general, the quench stage 3 is configured as a cooling tower. The cooling medium 6 used in the cooling tower is used in circulating form in a quench circuit. The circulation can be ensured by means of a suitable pump. The temperature of the cooling medium in the quench circuit can optionally be controlled by a heat exchanger. The circulation flow rate of the cooling medium in liters per hour, based on the mass flow rate of butadiene in grams per hour, may generally be 0.0001 to 5 l/g, preferably 0.001 to 1 l/g and more preferably 0.002 to 0.2 l/g.

The temperature of the biphasic cooling medium 6 in the column bottom may generally be 15 to 210° C., preferably 25 to 130° C., especially preferably 35 to 95° C. According to the temperature, pressure and water content of product gas 2, there may additionally be condensation of water in the first quench stage 3. Since the loading of the organic phase and the aqueous phase with secondary components increases over the course of time, a portion of the cooling medium can be drawn off from the circulation as purge stream 6b and the circulation rate can be kept constant by addition of organic phase 5a with lower loading and of aqueous phase 4a with lower loading. The ratio of output volume and addition volume depends on the steam loading of the product gas and the product gas temperature at the end of the first quench stage. The locations for the feeds and withdrawals are not subject to any further restriction. They may, for example, be upstream of or beyond the pump or the heat exchanger.

Figure 2:
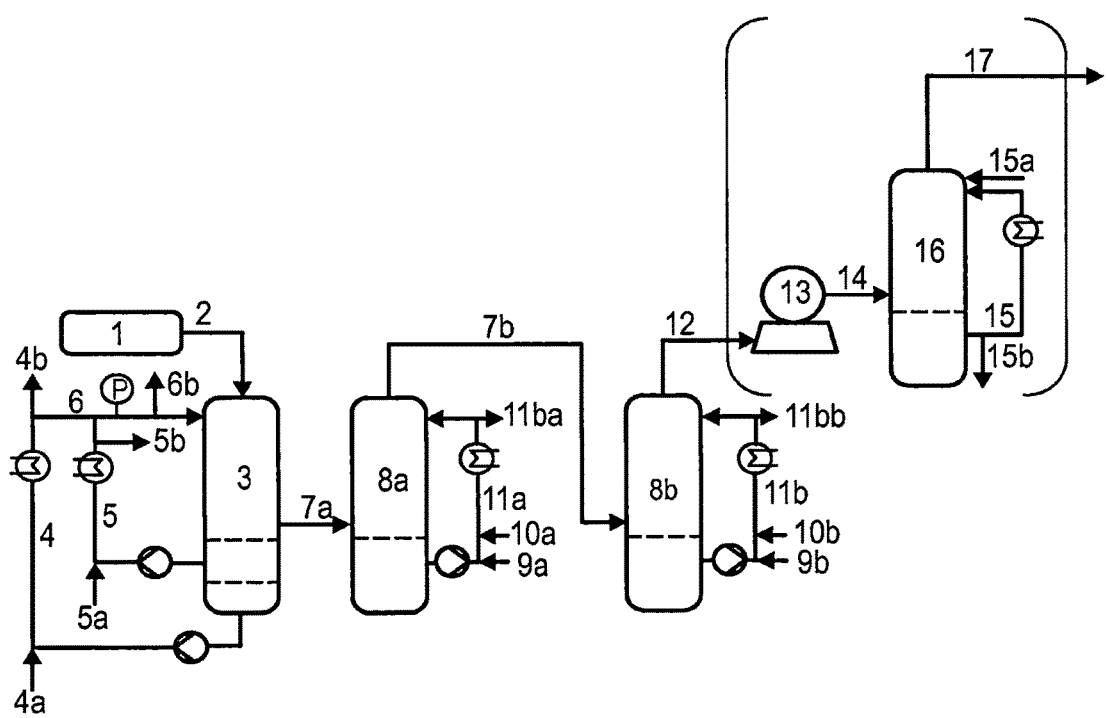
Figure 3:
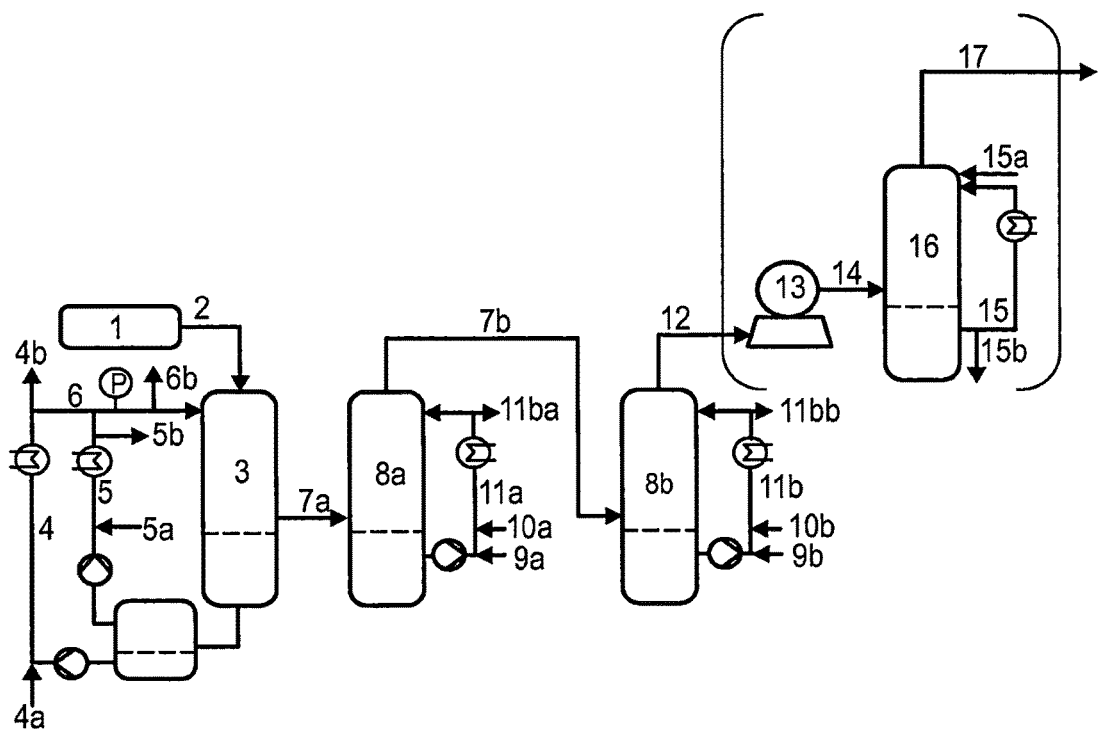

In the bottom of the quench stage 3, a predominantly aqueous phase 4 may form, which may additionally comprise water-soluble secondary components. This can, as shown in FIG. 2, be drawn off from the bottom of the quench stage 3 and recycled. The aqueous phase 4 may also, as shown in FIG. 3, be removed in an additional phase separator. This may, for example, be within the quench circuit. The aqueous phase 4 is at least partly recycled into the quench. The organic phase 5 too is at least partly recycled into the quench. Instead of or in addition to the purge stream 6b, it is also possible to remove a water purge stream 4b and an organic purge stream 5b.

In a preferred embodiment, the quench has two stages (comprising stages 3 and 8a according to FIGS. 1 to 3), i.e. stage Ca) and comprises two cooling stages Ca1) and Ca2) in which the product gas stream b is contacted with the cooling medium. According to the invention, at least the cooling medium in the first quench stage is biphasic. The two quench stages may be in separate cooling towers or in a common cooling tower.

In this case, the cooled product gas stream 7a, which may have been depleted of secondary components, is sent to a second quench stage 8a. In this stage, it is contacted again with a cooling medium 11a. The cooling medium 11a may be biphasic and may comprise an aqueous phase and an organic phase. However, it may also consist predominantly or exclusively of an organic solvent.

Preferably, the organic solvent comprises aromatic hydrocarbons, more preferably toluene, o-xylene, m-xylene, p-xylene, mesitylene, all the possible constitutional isomers of mono-, di- and triethylbenzene and all the possible constitutional isomers of mono-, di- and triisopropylbenzene, or mixtures thereof. Preference is also given to aromatic hydrocarbons having a boiling point at 1013.25 hPa of more than 120° C., or mixtures thereof. The organic solvent is preferably the same as in the first quench stage.

In general, the product gas, up to the gas outlet of the second quench stage 8a, is cooled to 5 to 100° C., preferably to 15 to 85° C. and more preferably to 20 to 70° C. The coolant can be fed in in countercurrent to the product gas. In this case, the temperature of the coolant medium 11a at the coolant inlet may be 5 to 100° C., preferably 15 to 85° C., especially preferably 30 to 70° C. The pressure in the second quench stage 8a is not particularly restricted, but is generally 0.01 to 4 bar (g), preferably 0.1 to 2 bar (g) and more preferably 0.2 to 1 bar (g), The second quench stage 8a is preferably configured as a cooling tower. The cooling medium 11a used in the cooling tower is used in circulating form in a quench circuit. The circulation flow rate 11a of the cooling medium in liters per hour, based on the mass flow rate of butadiene in grams per hour, may generally be 0.0001 to 5 l/g, preferably 0.001 to 1 l/g and more preferably 0.002 to 0.2 l/g.

Since the loading of the cooling medium 11a with secondary components increases over the course of time, a portion of the cooling medium can be drawn off from the circulation as purge stream 11ba and the circulation rate can be kept constant by addition of organic phase 10a with lower loading and optionally of aqueous phase 9a with lower loading.

The temperature of the cooling medium 11a in the column bottom may generally be 20 to 210° C., preferably 35 to 120° C., especially preferably 45 to 85° C. According to the temperature, pressure and water content of product gas 7a, there may additionally be condensation of water in the second quench stage 8a. In this case, an additional aqueous phase may form in the column bottom. The aqueous phase may also be removed in an additional phase separator. This may, for example, be within the quench circuit. The aqueous phase can be drawn off or at least partly recycled into the quench. Alternatively, the phase separator may be present, for example, in the purge stream 11ba.

The aqueous phase may at least partly be drawn off as a purge stream or at least partly be recycled into the quench. The organic phase may likewise at least partly be drawn off as a purge stream or at least partly be recycled into the quench.

The locations for the feeds and withdrawals in the circuits of the respective quench stages are not subject to any further restriction. They may, for example, be upstream of or beyond the pump or the heat exchanger. In addition, the location of the heat exchanger(s) in the quench circuit is not subject to any further restriction. In the case of partly phase-separated quench circuits, heat exchangers may be present in one or both circuits, or only in the recombined circuits. Alternatively, it is possible to entirely dispense with a heat exchanger, and the quench cooling may be accomplished solely through evaporation of the coolant. In addition, the location of the circulation pumps is not subject to any further restriction. In the case of a phase separator in the circulation stream, for example, a pump may be present upstream of the phase separator, or one pump may be present in each of the phase-separated circuits.

In order to achieve very good contact of product gas and cooling medium, internals may be present in the second quench stage 8a. Internals of this kind include, for example, bubble-cap, centrifugal and/or sieve trays, columns having structured packings, for example sheet metal packings having a specific surface area of 100 to 1000 $m^2/m^3$, such as Mellapak® 250 Y, and columns having random packings.

The coolant circulation streams of the quench stages may either be separate from one another or combined with one another. For example, a portion of stream 11ba may be supplied to stream 6 and at least partly replace streams 4a and/or 5a. The desired temperature of the circulation streams can be set by means of suitable heat exchangers.

In a preferred embodiment of the invention, the cooling stage Ca) is thus performed in two stages, in which case the organic solvent laden with secondary components from the second stage Ca2) is conducted into the first stage Ca1). The organic solvent withdrawn from the second stage Ca2) comprises a lower level of secondary components than the organic solvent withdrawn from the first stage Ca1).

Stage Ca) can also be performed in multiple stages in stages Ca1) to Can), more preferably in three stages Ca1), Ca2) and Ca3). In this case, at least a portion of the cooling medium may be fed as coolant to the second stage Ca2) after it has passed through the third stage Ca3).

In a particularly preferred embodiment, the quench has three stages (comprising stages 3, 8a and 8b according to FIGS. 1 to 3), i.e. stage Ca) comprises three cooling stages Ca1), Ca2) and Ca3) in which the product gas stream b is contacted with the cooling medium. According to the invention, at least the cooling medium in the first quench stage is biphasic. The three cooling stages may be in separate cooling towers or in a common cooling tower.

In this case, the cooled product gas stream 7a, which may have been depleted of secondary components, is sent to a second quench stage 8a, and the product gas stream 7b which may have been further depleted of secondary components is sent to a third quench stage 8b. In these quench stages, it is contacted again with a cooling medium 11b. The cooling medium 11b may be biphasic and may comprise an aqueous phase and an organic phase. However, it may also consist predominantly or exclusively of an organic solvent.

Preferably, the organic solvent in all three quench stages is the same.

The coolant circulation streams of the three quench stages may either be separate from one another or combined with one another.

In a particularly preferred embodiment of the invention, the cooling stage Ca) is thus conducted in three stages, in which case the organic solvent laden with secondary components from the second stage Ca2) is conducted into the first stage Ca1), and the organic solvent less heavily laden with secondary components from the third stage Ca3) is conducted into the second stage Ca2).

In a further embodiment, in the third cooling stage Ca3), a fresh cooling medium composed of an organic solvent or a mixture of organic solvent and water, said cooling medium being as yet unladen with the secondary components, is fed into the cooling stage in single pass and in countercurrent. Since the fresh cooling medium is as yet unladen with the secondary components to be removed in the quench stages, a further reduction in the secondary components unwanted in the product gas is achieved in the top product of the cooling tower.

In order to assure the liquid space velocity required for the design of the cooling tower in the cooling stage Ca3), the diameter chosen for this cooling stage Ca3) may be smaller than the diameter of the cooling stages Ca1) and Ca2). If the required liquid space velocity in the cooling stage Ca3) cannot be achieved by reducing the diameter, the liquid space velocity in this section is increased correspondingly by pumped circulation of the cooling medium.

In one embodiment of the invention, the first cooling stage Ca1) has a parallel and interchangeable configuration. In normal operation, only one of the two parallel cooling stages is operated, while the other is kept out of operation for cleaning operations or is available as a reserve.

In order to minimize the entrainment of liquid constituents from the quench into the offgas line, suitable construction measures, for example the installation of a demister, can be taken. In addition, high-boiling and other substances which are not separated from the product gas in the quench can be removed from the product gas through further construction measures, for example further gas scrubbing operations.

A gas stream 12 is obtained, in which comprises n-butane, 1-butene, 2-butenes and butadiene, with or without oxygen, hydrogen and water vapor, and small amounts of methane, ethane, ethene, propane and propene, isobutane, carbon oxides, inert gases and portions of the solvent used in the quench. In addition, traces of high-boiling components which have not been removed quantitatively in the quench may remain in this gas stream 12.

Subsequently, the gas stream b from the cooling step Ca), which has been depleted of high-boiling secondary components, is cooled in step Cb) in at least one compression stage Cba) and preferably in at least one cooling stage Cbb) by contacting with an organic solvent as a coolant.

Product gas stream 12 from the coolant quench (3, or preferably 3 and 8a, or preferably 3, 8a and 8b) is compressed in at least one compression stage 13 and subsequently cooled further in the cooling apparatus 16.

The compression and cooling of the gas stream 12 can be effected in one or more stages (n stages). In general, compression is effected overall from a pressure in the range from 1.0 to 4.0 bar (absolute) to a pressure in the range from 3.5 to 20 bar (absolute). Each compression stage is followed by a cooling stage in which the gas stream is cooled to a temperature in the range from 15 to 60° C. The cooling can be effected by direct or indirect heat exchange.

In order to directly cool stream 14 and/or to remove further secondary components from stream 14, stream 14 is contacted with a coolant 15. The cooling medium 15 may be monophasic or biphasic and may comprise an aqueous phase and an organic phase. The organic phase comprises, in a preferred execution, the same organic solvent as the quench coolants 6, 11a and 11b. As a result of the cooling, there is condensation of water and of organic solvent used in the quench and possibly of further secondary components. Since the loading of the coolant 15 with secondary components increases over the course of time, a portion of the laden coolant can be drawn off as stream 15b from the circuit, and the circulation rate of the coolant can be kept constant by adding coolant 15a with lower loading.

The coolant 15 can be cooled in a heat exchanger and recycled as coolant into the apparatus 16.

The condensate stream 15b can be fed into stream 5a and/or 10a and/or 10b, and hence recycled into the circulation stream 6 and/or 11a and/or 11b of the quench. As a result, the $C_4$ components absorbed in the condensate stream 15a can be brought back into the gas stream, and hence the yield can be increased.

What remains is a gas stream 17 comprising butadiene, 1-butene, 2-butenes, oxygen and water vapor, with or without low-boiling hydrocarbons such as methane, ethane, ethene, propane and propene, butane and isobutane, with or without carbon oxides and with or without inert gases. In addition, this product gas stream may also comprise traces of high-boiling components.

Suitable compressors are, for example, turbo compressors, rotary piston compressors and reciprocating piston compressors. The compressors may be driven, for example, with an electric motor, an expander or a gas or steam turbine. Typical compression ratios (outlet pressure: inlet pressure) per compressor stage are between 1.5 and 3.0 according to the design. The compressed gas is cooled with organic solvent-purged heat exchangers or organic quench stages, which may take the form, for example, of shell and tube, spiral or plate heat exchangers. The coolants used in the heat exchangers are cooling water or heat carrier oils. In addition, preference is given to using air cooling with use of blowers.

The gas stream 17 comprising butadiene, n-butenes, oxygen, low-boiling hydrocarbons (methane, ethane, ethene, propane, propene, n-butane, isobutane), with or without water vapor, with or without carbon oxides and with or without inert gases and with or without traces of secondary components is fed as an output stream to further processing.

Figure 4:
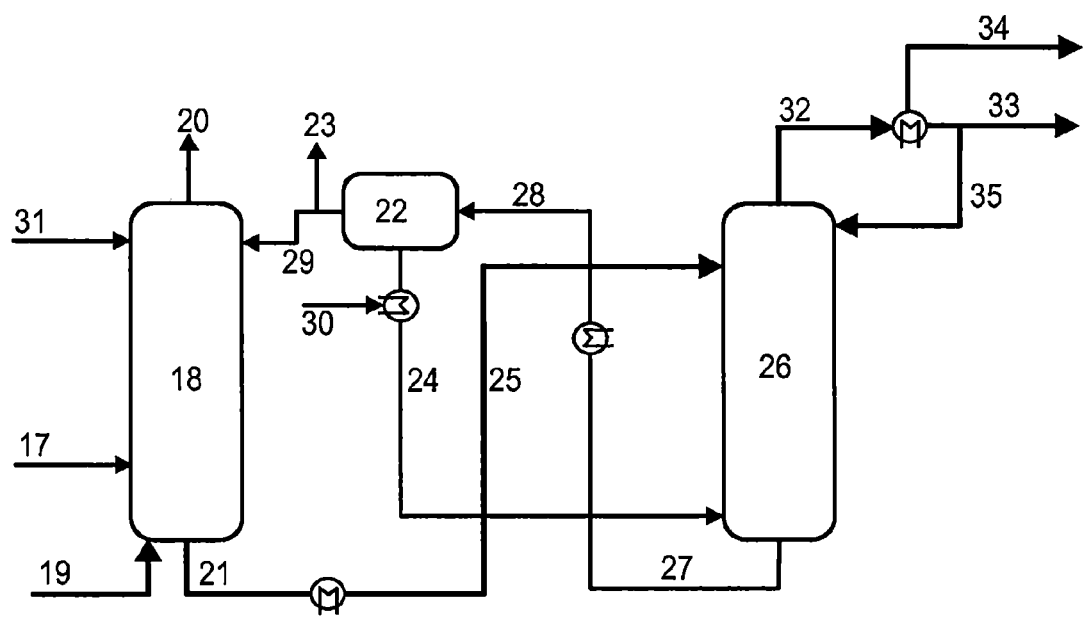

In a step D) shown in FIG. 4, uncondensable and low-boiling gas constituents comprising oxygen, low-boiling hydrocarbons (methane, ethane, ethene, propane, propene), carbon oxides and inert gases are separated in an absorption column as gas stream from the process gas stream 17 by absorption of the $C_4$ hydrocarbons in a high-boiling absorbent (29 and/or 31) and subsequent desorption of the $C_4$ hydrocarbons. Preferably, step D), as shown in FIG. 4, comprises steps Da to Dc):

Da) absorbing the $C_4$ hydrocarbons comprising butadiene and n-butenes in a high-boiling absorbent (29 and/or 31), giving an absorbent stream laden with $C_4$ hydrocarbons and the gas stream 20, Db) removing oxygen from the absorbent stream laden with $C_4$ hydrocarbons from step Da) by stripping with an uncondensable gas stream 19, giving an absorbent stream 21 laden with $C_4$ hydrocarbons, and Dc) desorbing the $C_4$ hydrocarbons from the laden absorbent stream, giving a $C_4$ product gas stream 32 consisting essentially of $C_4$ hydrocarbons.

For this purpose, in the absorption stage 18, gas stream 17 is contacted with an inert absorbent and the $C_4$ hydrocarbons are absorbed in the inert absorbent, giving an absorbent laden with $C_4$ hydrocarbons and an offgas 20 comprising the other gas constituents. In a desorption stage, the $C_4$ hydrocarbons are released again from the high-boiling absorbent.

The absorption stage can be conducted in any desired suitable absorption column known to those skilled in the art. The absorption can be effected by simply passing the product gas stream through the absorbent. However, it can also be effected in columns or in rotary absorbers. It is possible to work in cocurrent, countercurrent or crosscurrent. The absorption is preferably conducted in countercurrent. Suitable absorption columns are, for example, tray columns having bubble-cap, centrifugal and/or sieve trays, columns having structured packings, for example sheet metal packings having a specific surface area of 100 to 1000 $m^2/m^3$, such as Mellapak® 250 Y, and columns having random packings, Also useful, however, are trickle towers and spray towers, graphite block absorbers, surface absorbers such as thick-layer and thin-layer absorbers, and also rotary columns, pan scrubbers, cross-spray scrubbers and rotary scrubbers.

In one embodiment, the gas stream 17 comprising butadiene, n-butenes and the low-boiling and uncondensable gas constituents is supplied to an absorption column in the lower region. In the upper region of the absorption column, the high-boiling absorbent (29 and/or 31) is introduced.

Inert absorption media used in the absorption stage are generally high-boiling nonpolar solvents in which the $C_4$ hydrocarbon mixture to be separated off has a significantly higher solubility than the remaining gas components to be separated off. Suitable absorbents are comparatively nonpolar organic solvents, for example aliphatic $C_8$- to $C_{18}$-alkanes, or aromatic hydrocarbons such as the middle oil fractions from paraffin distillation, toluene or ethers having bulky groups, or mixtures of these solvents, to which a polar solvent such as dimethyl 1,2-phthalate may be added. Suitable absorbents are additionally esters of benzoic acid and phthalic acid with straight-chain $C_1$-$C_8$-alkanols, and what are called heat carrier oils, such as biphenyl and diphenyl ethers, chlorine derivatives thereof and triarylalkenes. A suitable absorbent is a mixture of biphenyl and diphenyl ether, preferably in the azeotropic composition, for example the commercially available Diphyl®. Frequently, this solvent mixture comprises dimethyl phthalate in an amount of 0.1% to 25% by weight.

In a preferred embodiment, the same solvent is used in the absorption stage Da) as in the cooling stage Ca).

Preferred absorbents are solvents having a dissolution capacity for organic peroxides of at least 1000 ppm (mg of active oxygen kg of solvent). In the preferred embodiment, the solvent used for the absorption is toluene, o-xylene, m-xylene, p-xylene, mesitylene or mixtures thereof.

At the top of the absorption column 18, an offgas stream 20 is drawn off, comprising essentially oxygen and low-boiling hydrocarbons (methane, ethane, ethene, propane, propene), with or without $C_4$ hydrocarbons (butane, butenes, butadiene), with or without inert gases, with or without carbon oxides and with or without water vapor. This stream can be supplied partly to the ODH reactor. It is thus possible, for example, to adjust the inlet stream of the ODH reactor to the desired $C_4$ hydrocarbon content.

At the bottom of the absorption column, in a further column, purging with a gas 19 discharges residues of oxygen dissolved in the absorbent. The remaining oxygen content should be sufficiently small that the stream 32 which comprises butane, butene and butadiene and leaves the desorption column comprises only a maximum of 100 ppm of oxygen.

The stripping of the oxygen in step Db) can be performed in any desired suitable column known to those skilled in the art. The stripping can be effected by simply passing uncondensable gases, preferably inert gases such as nitrogen, through the laden absorption solution. $C_4$ hydrocarbons additionally stripped out are washed back into the absorption solution in the upper portion of the absorption column 18, by passing the gas stream back into this absorption column. This can be effected either by means of pipe connection of the stripper column or direct mounting of the stripper column below the absorber column. This direct coupling can be effected since the pressure in the stripping column section and absorption column section is the same in accordance with the invention. Suitable stripping columns are, for example, tray columns having bubble-cap, centrifugal and/or sieve trays, columns having structured packings, for example sheet metal packings having a specific surface area of 100 to 1000 m²/m³, such as Mellapak® 250 Y, and columns having random packings. Also useful, however, are trickle towers and spray towers, and also rotary columns, pan scrubbers, cross-spray scrubbers and rotary scrubbers. Suitable gases are, for example, nitrogen or methane.

The absorbent stream 21 laden with $C_4$ hydrocarbons can be heated in a heat exchanger and then passed as stream 25 into a desorption column 26. In one process variant, the desorption step Dc) is performed by decompressing and/or heating the laden absorbent. The preferred process variant is the utilization of a vapor stream 24, which is supplied in the bottom of the desorption column 26.

The absorbent regenerated in the desorption stage is withdrawn as stream 27 from the desorption column 26 together with the condensed water. This biphasic mixture can be cooled in a heat exchanger and separated as stream 28 in a decanter 22 into an aqueous stream and an absorbent stream 29. The absorbent stream 29 is fed back to the absorber column 18, while the aqueous stream is evaporated in an evaporator and hence stream 24 is produced. Additionally or alternatively, additional water (stream 30) can also be evaporated in the evaporator.

Low boilers present in the process gas stream, for example ethane or propane, and high-boiling components such as benzaldehyde, maleic anhydride and phthalic anhydride, can accumulate in the circulation stream. In order to limit the accumulation, a purge stream 23 can be drawn off.

The $C_4$ product gas stream 32 consisting essentially of n-butane, n-butenes and butadiene comprises generally 20% to 80% by volume of butadiene, 0% to 80% by volume of n-butane, 0% to 10% by volume of 1-butene and 0% to 50% by volume of 2-butenes, where the total amount is 100% by volume. In addition, small amounts of isobutane may be present.

A portion of the condensed top discharge from the desorption column comprising principally $C_4$ hydrocarbons is recycled as stream 35 into the top of the column, in order to increase the separation performance of the column.

The liquid (stream 33) or gaseous (stream 34) $C_4$ product streams leaving the condenser are subsequently separated by extractive distillation in step E) with a butadiene-selective solvent into a stream comprising butadiene and the selective solvent, and a stream comprising n-butenes.

The extractive distillation can be performed, for example, as described in "Erdöl and Kahle-Erdgas-Petrochemie", volume 34 (8), pages 343 to 346, or "Ullmanns Enzyklopädie der Technischen Chemie", volume 9, 4th edition 1975, pages 1 to 18. For this purpose, the $C_4$ product gas stream is contacted with an extractant, preferably an N-methylpyrrolidone (NMP)/water mixture, in an extraction zone. The extraction zone generally takes the form of a scrubbing column comprising trays, random packings or structured packings as internals. This generally has 30 to 70 theoretical plates, in order that a sufficiently good separating action is achieved. Preferably, the scrubbing column has a re-scrubbing zone in the top of the column. This re-scrubbing zone serves for recovery of the extractant present in the gas phase with the aid of a liquid hydrocarbon return stream, for which the top fraction is condensed beforehand. The mass ratio of extractant to $C_4$ product gas stream in the feed to the extraction zone is generally 10:1 to 20:1. The extractive distillation is preferably operated at a bottom temperature in the range from 100 to 250° C., especially at a temperature in the range from 110 to 210° C., a top temperature in the range from 10 to 100° C., especially in the range from 20 to 70° C., and a pressure in the range from 1 to 15 bar, especially in the range from 3 to 8 bar. The extractive distillation column has preferably 5 to 70 theoretical plates.

Suitable extractants are butyrolactone, nitriles such as acetonitrile, propionitrile, methoxypropionitrile, ketones such as acetone, furfural, N-alkyl-substituted lower aliphatic acid amides such as dimethylformamide, diethylformamide, dimethylacetamide, diethylacetamide, N-formylmorpholine, N-alkyl-substituted cyclic acid amides (lactams) such as N-alkylpyrrolidones, especially N-methylpyrrolidone (NMP). In general, alkyl-substituted lower aliphatic acid amides or N-alkyl-substituted cyclic acid amides are used. Particularly advantageous are dimethylformamide, acetonitrile, furfural and especially NMP.

However, it is also possible to use mixtures of these extractants with one another, for example of NMP and acetonitrile, mixtures of these extractants with co-solvents and/or tert-butyl ethers, e.g. methyl tert-butyl ether, ethyl tert-butyl ether, propyl tert-butyl ether, n- or isobutyl tert-butyl ether. NMP is particularly suitable, preferably in aqueous solution, preferably with 0 to 20% by weight of water, more preferably with 7 to 10% by weight of water, especially with 8.3% by weight of water.

The top product stream from the extractive distillation column comprises essentially butane and butenes and small amounts of butadiene and is drawn off in gaseous or liquid form. In general, the stream consisting essentially of n-butane and 2-butene comprises up to 100% by volume of n-butane, 0% to 50% by volume of 2-butene, and 0% to 3% by volume of further constituents such as isobutane, isobutene, propane, propene and $C_5^+$ hydrocarbons.

The stream consisting essentially of n-butane and 2-butene can be fed fully or partly into the $C_4$ feed of the ODH reactor. Since the butene isomers in this recycle stream consist essentially of 2-butenes, and 2-butenes are generally oxidatively dehydrogenated more slowly to butadiene than 1-butene, this recycle stream can be catalytically isomerized before being fed into the ODH reactor. As a result, it is possible to adjust the isomer distribution in accordance with the isomer distribution present at thermodynamic equilibrium.

In a step F), the stream comprising butadiene and the selective solvent is distillatively separated into a stream consisting essentially of the selective solvent and a stream comprising butadiene.

The stream obtained at the bottom of the extractive distillation column generally comprises the extractant, water, butadiene and small proportions of butenes and butane and is fed to a distillation column. Butadiene can be obtained therein overhead or as a side draw. At the bottom of the distillation column, a stream comprising extractant, with or without water, is obtained, the composition of the stream comprising extractant and water corresponding to the composition as added to the extraction. The stream comprising extractant and water is preferably passed back into the extractive distillation.

If the butadiene is obtained via a side draw, the extraction solution thus drawn off is transferred into a desorption zone, and the butadiene is once again desorbed and re-scrubbed out of the extraction solution. The desorption zone may be configured, for example, in the form of a scrubbing column having 2 to 30 and preferably 5 to 20 theoretical plates, and optionally a rescrubbing zone having, for example, 4 theoretical plates. This re-scrubbing zone serves for recovery of the extractant present in the gas phase with the aid of a liquid hydrocarbon return stream, for which the top fraction is condensed beforehand. As internals, structured packings, trays or random packings are provided. The distillation is preferably performed at a bottom temperature in the range from 100 to 300° C., especially in the range from 150 to 200° C., and a top temperature in the range from 0 to 70° C., especially in the range from 10 to 50° C. The pressure in the distillation column is preferably in the range from 1 to 10 bar. In general, a reduced pressure and/or an elevated temperature exist in the desorption zone compared to the extraction zone.

The product of value stream obtained at the top of the column comprises generally 90 to 100% by volume of butadiene, 0 to 10% by volume of 2-butene and 0 to 10% by volume of n-butane and isobutane. For further purification of the butadiene, a further distillation can be performed in accordance with the prior art.

EXAMPLES

Dehydrogenation Experiments

Dehydrogenation experiments were conducted in a Miniplant reactor. The Miniplant reactor was a salt bath reactor having a length of 500 cm and an internal diameter of 29.7 mm, and a thermowell having an external diameter of 6 mm. On a catalyst support rested a 10 cm-long down-stream bed consisting of 60 g of steatite rings of geometry 7 mm×7 mm×4 mm (external diameter×length×internal diameter). This was followed by 2705 g of a undiluted eggshell catalyst (active composition content 19,6% by weight; bed height 384 cm, bed volume in the reactor 2552 ml) in the form of hollow cylinders of dimensions 7 mm×3 mm×4 mm (external diameter×length×internal diameter). The catalyst bed was adjoined by an 85 cm-long upstream bed consisting of 494 g of steatite rings of geometry 7 mm×7 mm×4 mm (external diameter×length×internal diameter).

The temperature of the reaction tube was controlled over its entire length with a salt bath which flowed around it. The reaction gas mixture used was a mixture comprising a total of 8% by volume of 1-, cis-2- and trans-2-butenes, small amounts of i-butene, 2% by volume of butanes (n- and isobutane), 12% by volume of oxygen, 5% by volume of water and remainder of nitrogen. The space velocity through the reaction tube was 5500 l (STP)/h of total gas. The temperature of the salt after the startup, during stable operation, was 374° C. The conversion of butenes was 85%, and the selectivity for butadiene was likewise about 85%. Secondary components detected comprise acetic acid, methacrolein, methyl vinyl ketone, methyl ethyl ketone, crotonaldehyde, acrylic acid, propionic acid, methacrylic acid, vinylcyclohexane, maleic anhydride, ethylbenzene, styrene, furanone, benzaldehyde, benzoic acid, phthalic anhydride, fluorenone, anthraquinone, formaldehyde, carbon monoxide and carbon dioxide.

The ODM offgas was cooled to 180° C. by means of a heat exchanger. It can be run directly to a flare or introduced laterally into the top of a quench column (see diagram). The quench column is 920 mm in length and has an internal diameter of 56 mm. After 300 mm and after 610 mm, Venturi nozzles having a central hole diameter of 8 mm are installed. The coolant is supplied from above to the top of the quench through a full-cone nozzle (Example 1, Comparative Example 1 and 2) or two full-cone nozzles (Example 2 and 3)(smallest free cross section 1.15 mm). The gas/coolant mixture passes through the quench column via the two Venturi nozzles, is collected at the bottom of the quench column and is conveyed as the quench circulation stream with the aid of a pump through a heat exchanger back to the top of the column. The pressure is measured on the pressure side of the pump. A portion of the laden coolant can be withdrawn from the circulation stream. In addition, coolant can be supplied to the circulation stream.

The product gas is sent to further workup.

Example 1

910 g/h of deionized water and 2017 g/h of mesitylene (1,3,5-trimethylbenzene) are supplied to the circulation stream of coolant around the quench column (see table). The circulation flow rate around the quench column is 60 l/h. The coolant level in the column bottom is kept constant by discharging coolant from the circulation system.

When the reactor has attained a stable state, the reactor offgas is diverted from the flare into the quench column. After a few hours, the coolant just upstream of the cone nozzle has a temperature of 75° C., and in the column bottom has a temperature of 71° C. The temperature in the gas space above the liquid coolant is measured at 73° C. The pressure in the coolant circuit is 1.5 bar gauge. The content of water vapor and mesitylene in the product gas which leaves the quench column is measured by online GC. The phase ratio in the quench circuit, expressed as mass of water to mass of mesitylene, is 0.45. The reactor and quench ran for more than 150 hours with a virtually constant coolant circulation flow rate, without any significant changes in the pressure.

Comparative Example 1

2000 g/h of mesitylene (1,3,5-trimethylbenzene) are supplied to the circulation stream. The circulation flow rate of coolant around the quench column is 60 l/h (see table). The amount of coolant in the column bottom is kept constant by discharging coolant from the circulation system.

When the reactor has attained a stable state, the reactor offgas is diverted from the flare into the quench column. After a few hours, the coolant just upstream of the cone nozzle has a temperature of 75° C., and in the bottom of the quench column has a temperature of 71° C. The temperature in the gas space above the liquid coolant is measured at 73° C. The pressure in the coolant circuit is 1.5 bar gauge. The content of water vapor and mesitylene in the product gas which leaves the quench column is measured by online GC. The phase ratio in the quench circuit, expressed as mass of water to mass of mesitylene, is less than 0.01.

Within a short time, the pressure in the circulation system begins to rise and the circulation flow rate begins to fall at the same time. After 17 h, the circulation flow has fallen to below 40 l/h, which causes an emergency shutdown of the plant. When the plant is opened up, solid deposits are found in the cone nozzle.

Comparative Example 2

1500 g/h of deionized water are supplied to the circulation stream. The circulation flow rate of coolant around the quench column is 60 l/h (see table). The coolant level in the column bottom is kept constant by discharging coolant from the circulation system.

When the reactor has attained a stable state, the reactor offgas is diverted from the flare into the quench column. After a few hours, the coolant just upstream of the cone nozzle has a temperature of 75° C., and in the column bottom has a temperature of 71° C. The temperature in the gas space above the liquid coolant is measured at 73° C. The pressure in the coolant circuit is 1.5 bar gauge. The content of water vapor and mesitylene in the product gas which leaves the quench column is measured by online GC. The phase ratio in the quench circuit, expressed as mass of water to mass of mesitylene, is greater than 185.

Within a short time, the pressure in the circulation system begins to rise and the circulation flow rate begins to fall at the same time. After 14 h, the circulation flow has fallen to below 40 l/h, which causes an emergency shutdown of the plant. When the plant is opened up, solid deposits are found in the cone nozzle.

Example 2

1112 g/h of deionized water and 2173 g/h of mesitylene (1,3,5-trimethylbenzene) are supplied to the circulation stream of coolant around the quench column (see table). The circulation flow rate around the quench column is 60 l/h through each of the 2 full-cone nozzles. The coolant level in the column bottom is kept constant by discharging coolant from the circulation system.

When the reactor has attained a stable state, the reactor offgas is diverted from the flare into the quench column. After a few hours, the coolant just upstream of the cone nozzle has a temperature of 75° C., and in the column bottom has a temperature of 73° C. The temperature in the gas space above the liquid coolant is measured at 75° C. The pressure in the coolant circuit is 1.5 bar gauge. The content of water vapor and mesitylene in the product gas which leaves the quench column is measured by online GC. The phase ratio in the quench circuit, expressed as mass of water to mass of mesitylene, is 0.53:1. The reactor and quench ran for more than 150 hours with a virtually constant coolant circulation flow rate, without any significant changes in the pressure.

Example 3

1314 g/h of deionized water and 2083 g/h of mesitylene (1,3,5-trimethylbenzene) are supplied to the circulation stream of coolant around the quench column (see table). The circulation flow rate around the quench column is 60 l/h through each of the 2 full-cone nozzles. The coolant level in the column bottom is kept constant by discharging coolant from the circulation system.

When the reactor has attained a stable state, the reactor offgas is diverted from the flare into the quench column. After a few hours, the coolant just upstream of the cone nozzle has a temperature of 75° C., and in the column bottom has a temperature of 73° C. The temperature in the gas space above the liquid coolant is measured at 75° C. The pressure in the coolant circuit is 1.5 bar gauge. The content of water vapor and mesitylene in the product gas which leaves the quench column is measured by online GC. The phase ratio in the quench circuit, expressed as mass of water to mass of mesitylene, is 0.99:1. The reactor and quench ran for more than 150 hours with a virtually constant coolant circulation flow rate, without any significant changes in the pressure.

|  | Example 1 | Comparative example 2 | Comparative example 3 | Example 2 | Example 3 |
| --- | --- | --- | --- | --- | --- |
| Feed rate of water vapor from reactor [g/h] | 664 | 664 | 664 | 587 | 629 |
| Feed rate of water to circulation system [g/h] | 910 | — | 1500 | 1112 | 1314 |

-continued

|  | Example 1 | Comparative example 2 | Comparative example 3 | Example 2 | Example 3 |
|---|---|---|---|---|---|
| Withdrawal rate of water vapor from quench column [g/h] | −1236 | >658 | −1236 | −1397 | −1418 |
| Withdrawal rate of water from circulation system [g/h] | −338 | <6 | −928 | −302 | −525 |
| Feed rate of mesitylene to circulation system [g/h] | 2017 | 2000 | <5 | 2173 | 2083 |

|  | Example 1 | Comparative example 2 | Comparative example 3 | Example 2 | Example 3 |
|---|---|---|---|---|---|
| Withdrawal rate of mesitylene vapor from quench column [g/h] | −1264 | −1264 | <5 | −1599 | −1553 |
| Withdrawal rate of mesitylene from circulation system [g/h] | −753 | 736 | <5 | −574 | −530 |
| Phase ratio in circuiation system [$g_{water}/g_{mesitylene}$] | 0.45 | <0.01 | >185 | 0.53 | 0.99 |
| Circulation flow rate [l/h] | 60 | 60 | 60 | 2.60 | 2.60 |

The invention claimed is:

1. A process for preparing butadiene from n-butenes, comprising the steps of:
   A) providing an input gas stream a comprising n-butenes,
   B) feeding the input gas stream a comprising n-butenes and a gas containing at least oxygen into at least one oxidative dehydrogenation zone and oxidatively dehydrogenating n-butenes to butadiene, giving a product gas stream b comprising butadiene, unconverted n-butenes, water vapor, oxygen, low-boiling hydrocarbons and high-boiling secondary components, with or without carbon oxides and with or without inert gases;
   Ca) cooling the product gas stream b by contacting with a cooling medium in at least one cooling zone, the cooling medium being at least partly recycled and having an aqueous phase and an organic phase of an organic solvent, wherein the organic solvent is selected from the group consisting of toluene, o-, m- and p-xylene, mesitylene, mono-, di- and triethylbenzene, mono-, di- and triisopropylbenzene and mixtures thereof, and the mass ratio of the aqueous phase to the organic phase in the cooling medium when it is fed into the cooling zones prior to the contacting with the product gas stream being from 0.15:1 to 10:1;
   Cb) compressing the cooled product gas stream b which may have been depleted of high-boiling secondary components in at least one compression stage, giving at least one aqueous condensate stream c1 and one gas stream c2 comprising butadiene, n-butenes, water vapor, oxygen and low-boiling hydrocarbons, with or without carbon oxides and with or without inert gases;
   D) removing uncondensable and low-boiling gas constituents comprising oxygen and low-boiling hydrocarbons, with or without carbon oxides and with or without inert gases, as gas stream d2 from the gas stream c2 by absorbing the $C_4$ hydrocarbons comprising butadiene and n-butenes in an absorbent, giving an absorbent stream laden with $C_4$ hydrocarbons and the gas stream d2, and then desorbing the $C_4$ hydrocarbons from the laden absorbent stream, giving a $C_4$ product gas stream d1,
   E) separating the $C_4$ product stream d1 by extractive distillation with a butadiene-selective solvent into a stream e1 comprising butadiene and the selective solvent and a stream e2 comprising n-butenes;
   F) distilling the stream e1 comprising butadiene and the selective solvent into a stream f1 consisting essentially of the selective solvent and a stream f2 comprising butadiene.

2. The process according to claim 1, wherein the mass ratio of the aqueous phase to the organic phase in the cooling medium used in step Ca) is from 0.18:1 to 2:1.

3. The process according to claim 2, wherein stage Ca) is conducted in three stages Ca1), Ca2) and Ca3) in three cooling zones.

4. The process according to claim 3, wherein an organic solvent laden with high-boiling secondary components from the second stage Ca2) is conducted into the first stage Ca1), and an organic solvent less heavily laden with high-boiling secondary components from the third stage Ca3) is conducted into the second stage Ca2).

5. The process according to claim 3, wherein a fresh cooling medium as yet unladen with the high-boiling secondary components is fed into the third cooling stage Ca3) in single pass and in countercurrent into the cooling stage.

6. The process according to claim 3, wherein the diameter of the cooling stage Ca3) is less than the diameter of the cooling stages Ca1) and Ca2).

7. The process according to claims 3, wherein the first cooling stage Ca1) has a parallel and interchangeable configuration.

8. The process according to claim 1, wherein the cooling medium is fed into the cooling zones through one or more nozzles.

9. The process according to claim 8, wherein a flow is generated in the nozzle(s), in which the Reynolds number Re of the two phases of the cooling medium is at least 100.

10. The process according to claim 1, wherein the volume-specific power input into the cooling medium is at least $10^3$ W/m$^3$.

11. The process according to claim 1, wherein the coefficient of variation for each component of the cooling medium on entry into the cooling zones is less than 1.

12. The process according to claim 1, wherein stage Cb) comprises at least one compression stage Cba) and at least one cooling stage Cbb).

13. The process according to claim 12, wherein the coolant in the cooling stage Cbb) comprises the same organic solvent which is used in stage Ca) as the organic phase of the cooling medium.

14. The process according to claim 1, wherein stage Cb) comprises a plurality of compression stages Cba1) to Cban) and cooling stages Cbb1) to Cbbn).

15. The process according to claim 1, wherein step D) comprises steps Da) to Dc):
Da) absorbing the $C_4$ hydrocarbons comprising butadiene and n-butenes in a high-boiling absorbent, giving an absorbent stream laden with $C_4$ hydrocarbons and the gas stream d2,
Db) removing oxygen from the absorbent stream laden with $C_4$ hydrocarbons from step Da) by stripping with an uncondensable gas stream, and
Dc) desorbing the $C_4$ hydrocarbons from the laden absorbent stream, giving a $C_4$ product gas stream d1 comprising less than 100 ppm of oxygen.

16. The process according to claim 15, wherein the high-boiling absorbent used in step Da) is an aromatic hydrocarbon solvent.

* * * * *